(12) United States Patent
Lee et al.

(10) Patent No.: US 8,797,536 B2
(45) Date of Patent: *Aug. 5, 2014

(54) PORTABLE DIGITAL READER FOR URINALYSIS

(75) Inventors: Dae Sik Lee, Daejeon (KR); Hyun Woo Song, Daejeon (KR); Byoung Goo Jeon, Daejeon (KR); Moon Youn Jung, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 111 days.

This patent is subject to a terminal disclaimer.

(21) Appl. No.: 13/390,506

(22) PCT Filed: Mar. 5, 2010

(86) PCT No.: PCT/KR2010/001387
§ 371 (c)(1),
(2), (4) Date: Feb. 14, 2012

(87) PCT Pub. No.: WO2011/030983
PCT Pub. Date: Mar. 17, 2011

(65) Prior Publication Data
US 2012/0162653 A1    Jun. 28, 2012

(30) Foreign Application Priority Data
Sep. 9, 2009  (KR) .................. 10-2009-0084911

(51) Int. Cl.
*G01N 21/59*    (2006.01)
(52) U.S. Cl.
USPC ........................................ 356/436; 73/61.48
(58) Field of Classification Search
USPC .................. 356/432–440; 73/61.48, 1.02
See application file for complete search history.

(56) References Cited

U.S. PATENT DOCUMENTS 6,335,203 B1   1/2002  Patel et al.
7,576,861 B2 *  8/2009  Gilbert et al. ................ 356/436
(Continued)

FOREIGN PATENT DOCUMENTS

CN    101115436 A     1/2008
EP     1 857 804 A2   11/2007
(Continued)

OTHER PUBLICATIONS

Dae-Sik Lee et al., "An Optical Absorbance-based Mult-analytes Detector Using LEDs and an Optical Fiber for a Handheld Digital Urine Reader", 2008 International Symposium and Annual Fall Meeting of the Korean BioChip Society, 2008, pp. 234.

(Continued)

*Primary Examiner* — Hoa Pham

(57) ABSTRACT

The present invention relates to a portable digital reader for reading an analysis target chip including a plurality of test areas. The reader comprises: a light emitting section having light emitting elements for radiating light; an integral optical splitter for uniformly distributing the light from the light emitting section to each test area of the analysis target chip; a light receiving section for receiving light reflected from each test area so as to convert the same into electric signals; and a measuring section for measuring concentration according to the electric signals obtained from the light receiving section. Therefore, it is possible to prevent the generation of errors in signal measurement due to optical distribution failure by assembling branch sections of the optical splitter under the control of the number of the branch sections according to the number of test items in a test strip.

14 Claims, 2 Drawing Sheets

(56) References Cited

U.S. PATENT DOCUMENTS

| | | | |
|---|---|---|---|
| 2006/0240375 A1* | 10/2006 | Soukos et al. | 433/29 |
| 2007/0231208 A1 | 10/2007 | Tanaka et al. | |
| 2007/0287182 A1 | 12/2007 | Morris et al. | |
| 2008/0019867 A1 | 1/2008 | Johnson et al. | |
| 2008/0174768 A1* | 7/2008 | Belz | 356/73 |
| 2010/0157300 A1* | 6/2010 | Lee et al. | 356/402 |
| 2012/0152002 A1* | 6/2012 | Lee et al. | 73/61.48 |

FOREIGN PATENT DOCUMENTS

| | | |
|---|---|---|
| KR | 1020050072015 A | 7/2005 |
| KR | 1020060032778 A | 4/2006 |
| KR | 10-2007-0006304 A | 1/2007 |
| KR | 1020080052349 A | 6/2008 |
| KR | 20-2009-0002043 U | 3/2009 |
| KR | 1020100073061 A | 7/2010 |
| WO | WO 95/13531 A1 | 5/1995 |
| WO | WO 2006/054116 A2 | 5/2006 |
| WO | WO 2006/083880 A2 | 10/2006 |
| WO | WO 2008/069554 A1 | 6/2008 |

OTHER PUBLICATIONS

International Search Report for PCT/KR2010/001387 filed on Mar. 5, 2010.

* cited by examiner

PORTABLE DIGITAL READER FOR URINALYSIS

TECHNICAL FIELD

The present invention relates to a digital reader for urine analysis and, more particularly, to a portable digital reader for urine analysis, which irradiates a plurality of test parts to detect a reaction.

BACKGROUND ART

In general, urine analysis strip chips have a variety of individual test items. Particularly, these test items include occult blood, bilirubin, urobilinogen, ketone body, protein, nitrite, glucose, pH, specific gravity, white blood cell, vitamin C, and so on. Urinalysis using test paper is a semi-quantitative test that primarily screens various body diseases, and can test for abnormalities in their early stages in the body. With this test, it is easy to sample urine, gives no burden to test patients, and allows its results to be immediately determined, so it has become highly utilized. The urine analysis strip chips exhibit test results to the test patient so as to be able to check for abnormalities of the above-mentioned relevant items with the naked eye.

DISCLOSURE

Technical Problem

Since strip chips by nature use testing parts for the respective test items which are attached to a plastic film, they may have a color region where it is difficult to discriminate a change in color shown as a result of the testing with the naked eye. Thus, the strip chips have a drawback in which test accuracy may be lowered as in the case in which the discrimination in the same color pattern varies depending on an individual such as one who is color blind.

Thus, a reader is used to read information out of these strip chips. The readers, which are on the market at present and are used in hospitals, are bulky and expensive. As such, there is a pressing need to develop diagnostic readers of new concept capable of testing and monitoring health of the public at large anywhere anytime. To this end, readers using light emitting and receiving elements are presented. However, these readers use one light source for the light emitting element, and so the light is not uniformly and stably distributed to the numerous test parts of one strip chip.

Technical Solution

The present invention is directed to a portable digital reader for urine analysis, capable of uniformly and stably distributing light to a plurality of test parts using a single light source.

An aspect of the present invention provides a portable digital reader for urine analysis, in which a chip, which is intended for analysis and has a plurality of test regions, is read out. The portable digital reader includes a light emitter including light emitting elements and emitting light, an integrated light distributor uniformly distributing the light from the light emitter to each test region of the chip, a light receiver receiving the light reflected from each test region and converting the received light into an electric signal, and a measuring part measuring concentration based on the electric signal received from the light receiver.

In exemplary embodiments, the light distributor may include a stem part extending from the light emitter in a traveling direction of the light, and a plurality of branch parts extending from the stem part in a downward direction.

In exemplary embodiments, the light distributor may further include an organic or inorganic material for helping achieve total reflection on an upper surface of the stem part thereof.

In exemplary embodiments, the light distributor may be configured such that an upper surface of the stem part thereof has a predetermined curvature so as to totally reflect the light incident on the stem part toward the branch parts.

In exemplary embodiments, the number of branch parts may be equal to or greater than that of the test regions.

In exemplary embodiments, the light distributor may be formed of a polymer having a refractive index higher than that of air.

In exemplary embodiments, the polymer may be one selected from polymethyl methacrylate (PMMA), polyimide (PI), polycarbonate (PC)), and cyclo olefin copolymer (COC).

In exemplary embodiments, the light emitter may include three-color light emitting diodes.

In exemplary embodiments, the measuring part may include a controller, which controls the light emitter to be driven in a switching mode when the chip is mounted, receives and stores the electric signal from the light receiver, and performs data analysis.

In exemplary embodiments, the light receiver may include a plurality of photodiodes. In exemplary embodiments, the plurality of photodiodes may be separated from one another by sidewalls.

In exemplary embodiments, the portable digital reader may further include a telecommunication unit, which is provided to send results analyzed by the controller to a remote terminal.

In exemplary embodiments, the portable digital reader may further include a display part for displaying results analyzed by the controller.

Advantageous Effects

According to the exemplary embodiment of the present invention, a light distributor is assembled by adjusting the number of branch parts thereof according to the number of test items within a test strip, so that it is possible to prevent an error caused by poor distribution of light when a signal is measured.

DESCRIPTION OF DRAWINGS

The above and other features and advantages of the present invention will become more apparent to those of ordinary skill in the art by describing in detail preferred embodiments thereof with reference to the attached drawings in which.

MODE FOR INVENTION

Figure 1:
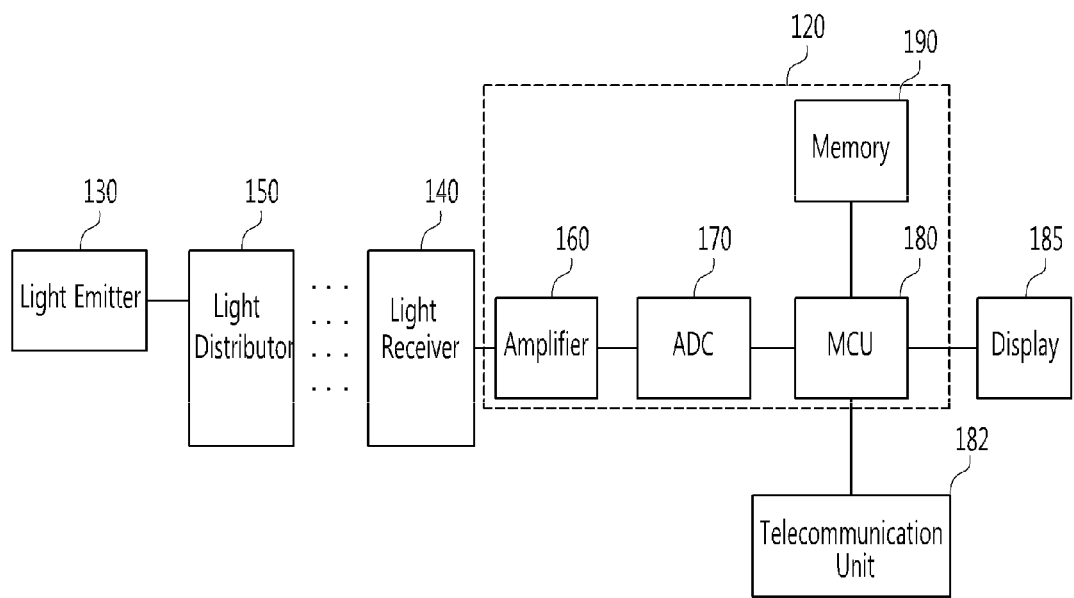
FIG. 1 is a block diagram illustrating a portable digital reader for urine analysis according to an exemplary embodiment of the present invention.

The present invention will be described more fully hereinafter with reference to the accompanying drawings, in which exemplary embodiments of the invention are shown. This invention may, however, be embodied in different forms and should not be construed as limited to the embodiments set forth herein. In order to keep the following description of the present invention clear and concise, detailed descriptions of known functions and components may be omitted. When any element of the invention appears in more than one drawing, it is denoted by the same reference numeral in each drawing.

It will be understood that, throughout the specification, unless explicitly stated to the contrary, the term "comprise" and its conjugations such as "comprises" and "comprising" should be interpreted as including any stated elements but not necessarily excluding other elements. In addition, the terms "section," "device," and "module" used herein refer to a unit which can be embodied as hardware, software, or a combination thereof, for processing at least one function and performing an operation.

FIG. 1 is a block diagram illustrating a portable digital reader for urine analysis according to an exemplary embodiment of the present invention.

Figure 2:
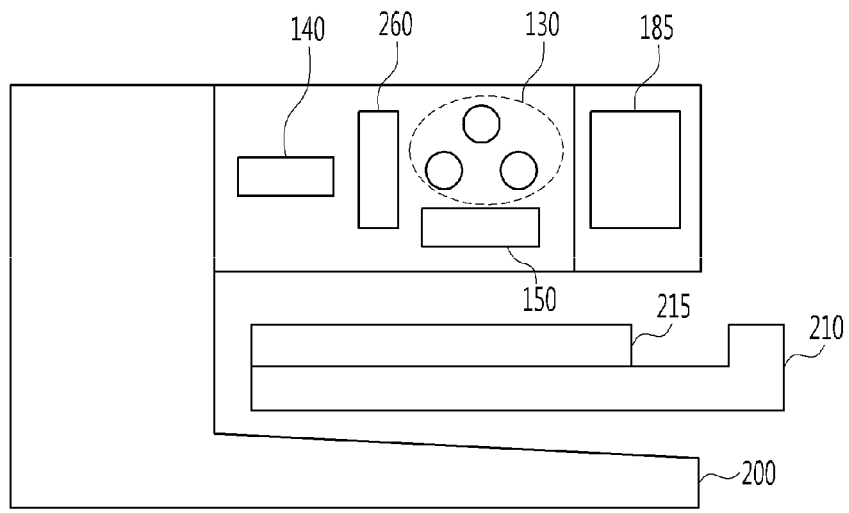
FIG. 2 illustrates a configuration for explaining the structure of a portable digital reader for urine analysis according to an exemplary embodiment of the present invention.

FIG. 2 illustrates a configuration for explaining the structure of a portable digital reader for urine analysis according to an exemplary embodiment of the present invention. Referring to FIG. 1, the portable digital reader for urine analysis includes a light emitter 130 having a three-color light source, a light distributor 150 uniformly transmitting light from the light emitter 130 to each region of a strip chip, a light receiver 140 receiving the light, which is transmitted from the light emitter 130 and is reflected from the strip chip, to perform photoelectric conversion into an electric signal, and a measuring part 120, which measures concentration based on the electric signal received from the light receiver 140.

Further, this digital reader further includes a telecommunication unit 182, and a display 185.

The measuring part 120 includes an amplifier 160, an analog-to-digital converter (ADC) 170, a micro control unit (MCU) 180, a memory 190.

The amplifier 160 amplifies the electric signal received from the light receiver 140 and sends it to the ADC 170. The ADC 170 converts the amplified signal into a digital signal and sends it to the MCU 180.

The MCU 180 analyzes the digital signal from the ADC 170. Here, the MCU 180 reads chromaticity coordinates of the digital signal to check for a reaction.

Meanwhile, the MCU 180 controls the light emitter 130 in a switching mode.

The memory 190 stores a program driven by the MCU 180, and temporarily stores data calculated by the MCU 180. The display 185 displays the data calculated by the MCU 180, and includes a liquid crystal display, or the like.

The telecommunication unit 182 sends results read out by the MCU 180 to a remote clinic such as a hospital or a public health center, and may include a radio frequency identification system (RFID) chip as a telecommunication module. In this case, the MCU 180 records the results on the RFID chip. When a user intends to send the results to the remote clinic, the user reads the results out of the RFID chip using a wired or wireless terminal on which an RFID reader is mounted, and sends it to a remote terminal.

Further, this reader may include a fluid control module (not shown), which is configured to move, stop, and mix a microfluid in order to make efficient analysis in a bio-chip or strip chip.

The fluid control module includes a channel capable of moving, mixing, and stopping a relevant solution in order to facilitate the analysis of a biological sample, a storage tank storing the fluid, a pump transferring the fluid, a valve controlling the transfer of the fluid, and a mixer for fluid control. In order to move, stop, and mix the fluid, a variety of existing driving means such as an electrostatic motor, a piezoelectric pump, a hydraulic or pneumatic pressure, ultrasonic waves, etc. may be used.

Meanwhile, referring to FIG. 2, the digital reader having the blocks shown in FIG. 1 includes a body 200 and a support 210.

In FIG. 2, the digital reader according to the present invention is to be viewed from the side. The body 200 is formed in a C shape, and the support 210 is taken into or out of a space between opposite lower and upper surfaces of the body 200.

The support 210 has a bio-chip 215 mounted thereon and moves into the body 200. The body 200 is equipped with a light emitter 130 irradiating each test region of the bio-chip 215, a light receiver 140, a sidewall 260, and a light distributor 150 at an upper portion thereof. Further, the body 200 may include a display 185, which displays test results.

The light emitter 130 is configured to combine three-color light emitting diodes (LEDs), i.e. red, blue, and green LEDs.

The three-color light source elements of the light emitter 130 may be discontinuously controlled in a switching mode. For example, the red LED may be operated for a predetermined time, and the signal value R of a photodiode reacting on the light of the red LED may be temporarily stored. Next, the green LED may be operated for a predetermined time, and the signal value G of the photodiode reacting on the light of the green LED may be temporarily stored. Finally, the blue LED may be operated for a predetermined time, and the signal value B of the photodiode reacting on the light of the blue LED may be temporarily stored. By using these stored R, G, and B values, concentration of a target specimen is measured by a value of hue, and it can be checked by a value of intensity whether or not the chip is mounted or the reader is abnormal.

The light receiver 140 may use a silicon sensor such as a silicon photodiode or a phototriode. These sensors may be configured in an array, so that it is possible to secure sensitivity and easy mounting of the bio chip.

The sidewall 260 is provided between the light emitter 130 and the light receiver 140 in order to efficiently discriminate the light, particularly, between the light receiving elements of the light receiver 140.

The light distributor 150 will be described below in detail.

Meanwhile, the strip chip or the bio chip 215 is inserted into the support 210 having an elastic member installed on the reader, and then is fixed in a recess formed in a lever when arriving at a designated position.

Here, the bio chip 215 is provided thereon with either a chip fixing structure coupled with a spring mounted on the reader or a polymer layer having elasticity. As such, the chip fixing structure helps keep an interval between the chip and the light distributor constant when the urine analysis is made, and allows measurement of the bio chip 215 regardless of external impact or fluctuation.

Operation of the reader having this configuration will now be described.

When the bio chip 215 is inserted into the reader, a switch is turned on, and thus a signal informing that the bio chip 215 is inserted is applied to the MCU 180. When the insertion signal of the bio chip 215 is applied, the MCU 180 determines that the bio chip 215 is inserted into the reader, thereby applying power to the light emitter 130 made up of three-color LEDs.

Here, the MCU 180 applies the power such that the three-color LEDs are discontinuously switched on.

Thereby, the light emitter 130 emits light. The emitted light passes through the light distributor 150, is reflected from each test region of the bio chip 215, and is received by the light receiver 140.

First, whenever the reader is powered on, the signal is compensated for the light source by reading a value of the signal received by the light receiver 140 with respect to initial light source signal intensity of each of the three-color LEDs. For this compensation, a compensator for a white or black color acting as a separate standard color may be further installed in the reader. Thereby, it is possible to obtain precision and reproducibility of the measured signal.

The light receiver 140 converts the received optical signal into an electric signal. The electric signal converted by the light receiver 140 is subject to signal processing and analysis by the MCU 180. The analysis results are displayed through the display 185.

Further, the MCU 180 records the readout result on the RFID chip, or enables a user to send the results to a desired remote terminal through a mobile communication modem. Hereinafter, the light distributor of the digital reader will be described with reference to FIGS. 3 and 4.

Figure 3:
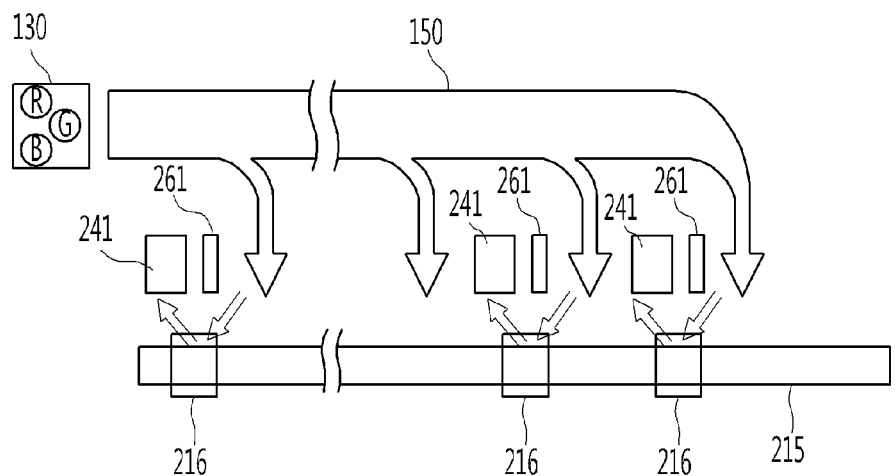
FIG. 3 is a configuration view explaining the distribution of light in a portable digital reader for urine analysis according to an exemplary embodiment of the present invention.
Figure 4:
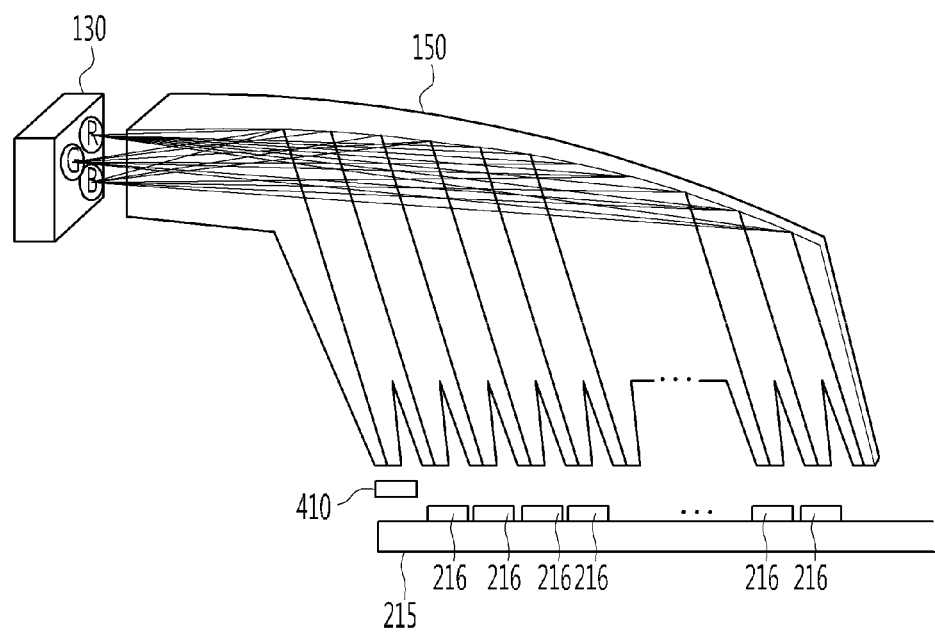
FIG. 4 illustrates an example of a light distributor for the light distribution of FIG. 3.

FIG. 3 is a configuration view explaining the distribution of light in a portable digital reader for urine analysis according to an exemplary embodiment of the present invention. FIG. 4 illustrates an example of a light distributor for the light distribution of FIG. 3.

The light distributor 150 includes an integrated module for distributing light between the light emitter 130 and the light receiver 140.

One bio-chip or strip chip 215 includes a plurality of test regions 216 according to a target material intended for detection.

As in FIG. 3, the light receiver 140 includes a plurality of photoelectric elements 241 corresponding to the respective test regions 216.

The photoelectric elements 241 are separated by respective sidewalls 261.

The light distributor 150 is disposed between the three-color light emitter 130 and the test regions 216, receives the light from the light emitter 130, and reflects the light such that the light can be uniformly distributed to the test regions 216.

In detail, as in FIG. 4, the light distributor 150 includes a stem part extending from the light emitter 130 in a traveling direction of the light, and a plurality of branch parts extending from the stem part in a downward direction.

The branch parts are opposite to the respective test regions 216 at free ends thereof.

More specifically, the branch parts are equal in number to the test regions 216. When the light distributor further includes a compensator 410 compensating for a white or black color as in FIG. 4, the light distributor 150 may include the branch parts, which outnumber the test regions 216 by one.

At this time, an upper wall of the stem part is inclined with a predetermined curvature. Owing to this curvature, the light of the light emitter 130 travels straight along the stem part, is totally reflected on different portions of the upper wall of the stem part, and is incident on the branch parts.

Here, the upper wall of the stem part may further include an organic or inorganic material for helping achieve total reflection.

Further, the curvature for distributing and focusing is determined by a distance between the branch parts, i.e., a distance between the test regions 216 for detection.

This light distributor 150 is an integrated structure for reflection, or focusing, and is formed of a polymer having a refractive index higher than that of air.

This high-refractive index polymer may include polymethyl methacrylate (PMMA), polyimide (PI)), polycarbonate (PC), cyclo olefin copolymer (COC), poly ethylene terephthalate (PET), polypropylene (PP) or the like.

The integrated module of the light distributor 150 may be formed using an existing polymer micromachining technique such as injection molding, hot embossing, casting, or soft lithography, or conventional mechanical technique like CNC (computer numerical control) processing.

The light distributor 150 may be designed from one test strip to ten or more test strips. Even when the number of test items increases within the test strip, the light distributor 150 is assembled by adjusting only the number of branch parts thereof, so that it is possible to prevent an error caused by distribution of light when the signal is measured. The exemplary embodiment of the present invention described above can also be implemented as a computer program, or as a recording medium on which a computer program is recorded. This will be easily implemented from the disclosure of the above-mentioned exemplary embodiments of the present invention by those skilled in the art.

While the invention has been shown and described with reference to certain exemplary embodiments thereof, it will be understood by those skilled in the art that various changes in form and details may be made therein without departing from the spirit and scope of the invention as defined by the appended claims.

The invention claimed is:

1. A portable digital reader for reading a target chip including a plurality of test regions, the portable digital reader comprising:
   a support configured to receive the target chip;
   a light emitter including light emitting elements and emitting light;
   an integrated light distributor comprising:
      a stem part extending from the light emitter in a traveling direction of the light, the stem part being configured to reflect light from the light emitter; and
      a plurality of branch parts extending toward the support from the stem part;
      wherein a surface of the stem part has a predetermined curvature based on a distance between branch parts to totally reflect the light incident on the stem part toward the branch parts, the light incident on the stem part being distributed to the target chip through a branch part;
   a light receiver configured to receive the light, which is reflected from each test region, and convert the received light into an electric signal; and
   a measuring part configured to measure a concentration based on the electric signal received from the light receiver.

2. The portable digital reader according to claim 1, wherein a surface of the stem part of the light distributor includes an organic or inorganic material for achieving total reflection.

3. The portable digital reader according to claim 1, wherein a number of the branch parts is equal to a number of the test regions, and wherein each of the branch parts correspond to a test region of the target chip respectively.

4. The portable digital reader according to claim 1, wherein the light distributor is formed of a polymer having a refractive index higher than a refractive index of air.

5. The portable digital reader according to claim 4, wherein the polymer is one selected from polymethyl methacrylate (PMMA), polyimide (PI), polycarbonate (PC)), cyclo olefin copolymer (COC), poly ethylene terephthalate (PET), and polypropylene (PP).

6. The portable digital reader according to claim 1, wherein the light emitter includes three-color light emitting diodes.

7. The portable digital reader according to claim 1, wherein the measuring part includes a controller, which controls the light emitter to be driven in a switching mode when the target chip is mounted on the support, receives and stores the electric signal from the light receiver, and performs data analysis.

8. The portable digital reader according to claim 7, further comprising a telecommunication unit configured to send results analyzed by the controller to a remote terminal.

9. The portable digital reader according to claim 7, further comprising a display part configured to display results analyzed by the controller.

10. The portable digital reader according to claim 7, wherein the light emitter includes three-color light emitting diodes, and
   wherein, in the switching mode, each of the light emitting diodes operates individually for a predetermined time.

11. The portable digital reader according to claim 1, wherein the light receiver includes a plurality of photodiodes.

12. The portable digital reader according to claim 11, wherein the plurality of photodiodes are separated from one another by sidewalls.

13. The portable digital reader according to claim 1, further comprising a body including an upper portion, a lower portion, and a space therebetween,
   wherein the support is provided in the space,
   wherein the light distributor is provided in the upper portion of the body and extends over a length of the support, and
   wherein the branch parts extend at an angle from the stem part and towards the support.

14. The portable digital reader according to claim 1, wherein the light distributor further includes a compensator configured to compensate for a white or black color, wherein a number of the branch parts is one more than a number of the test regions, and wherein the light incident on the stem part is distributed to each test region of the target chip through a corresponding branch part.

* * * * *